US008486312B2

(12) United States Patent
Melzig et al.

(10) Patent No.: US 8,486,312 B2
(45) Date of Patent: Jul. 16, 2013

(54) PHOTOCHROMIC NAPHTHOPYRANS HAVING A DOUBLE-BRIDGED TERPHENYL SUB-UNIT

(75) Inventors: Manfred Melzig, Wessling (DE); Yven Rohlfing, Munich, DE (US); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 346 days.

(21) Appl. No.: 12/937,414

(22) PCT Filed: Apr. 29, 2009

(86) PCT No.: PCT/EP2009/003113
§ 371 (c)(1),
(2), (4) Date: Dec. 7, 2010

(87) PCT Pub. No.: WO2009/132842
PCT Pub. Date: Nov. 5, 2009

(65) Prior Publication Data
US 2011/0081482 A1    Apr. 7, 2011

(30) Foreign Application Priority Data

Apr. 30, 2008  (DE) .................. 10 2008 021 823

(51) Int. Cl.
*G02B 5/23* (2006.01)
*B05D 5/06* (2006.01)
*C07D 311/94* (2006.01)

(52) U.S. Cl.
USPC ............ 252/586; 427/164; 549/382; 549/389

(58) Field of Classification Search
USPC .................... 252/586; 427/164; 549/382, 389
See application file for complete search history.

(56) References Cited

U.S. PATENT DOCUMENTS

| 6,506,538 | B1 | 1/2003 | Breyne et al. |
| 6,558,583 | B2 * | 5/2003 | Breyne et al. ................. 252/586 |
| 2002/0197562 | A1 * | 12/2002 | Breyne et al. ............ 430/270.15 |
| 2004/0094753 | A1 * | 5/2004 | Izumi et al. ................... 252/586 |
| 2005/0092972 | A1 | 5/2005 | Chan et al. |
| 2005/0258408 | A1 * | 11/2005 | Molock et al. ................. 252/586 |
| 2010/0230648 | A1 | 9/2010 | Izumi et al. |

FOREIGN PATENT DOCUMENTS

| FR | 2783248 | 3/2000 |
| WO | 00/15628 | 3/2000 |
| WO | 00/77007 | 12/2000 |
| WO | 2005047277 | 5/2005 |
| WO | 2007/054240 | 5/2007 |

OTHER PUBLICATIONS

PCT/EP2009/003113; English Translation of PCT International Preliminary Report on Patentability dated Nov. 9, 2010.
PCT/EP2009/003113; PCT International Search Report dated Jul. 21, 2009.
Official Action for Japanese Patent Application No. 2011-506610, dated Apr. 16, 2013.

* cited by examiner

Primary Examiner — James Lin
(74) Attorney, Agent, or Firm — Renner, Otto, Boisselle & Sklar, LLP

(57) ABSTRACT

The present invention relates to photochromic naphthopyrancs having a double-bridged terphenyl sub-unit, and to the use thereof in plastics of all types, particularly for ophthalmic purposes.

20 Claims, 2 Drawing Sheets

PHOTOCHROMIC NAPHTHOPYRANS HAVING A DOUBLE-BRIDGED TERPHENYL SUB-UNIT

Figure 1:
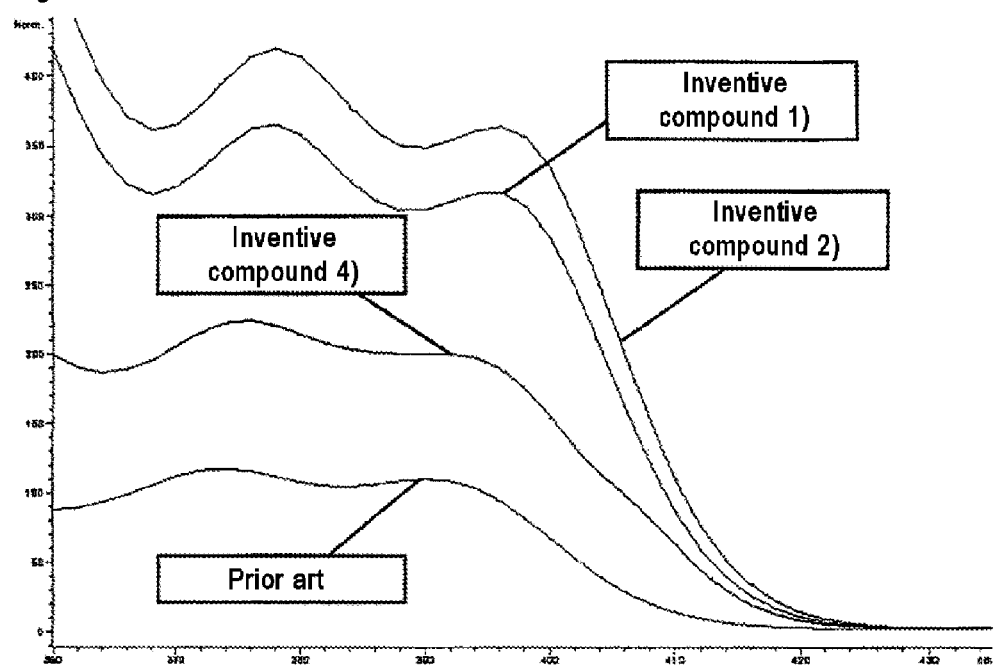

The present application is a U.S. National Stage Application based on and claiming priority under 35 U.S.C. §371 to International Application No. PCT/EP2009/003113, filed 29 Apr. 2009, which in turn claims priority to German Application No. 10 2008 021 823.5, filed 30 Apr. 2008, the entireties of both of which are hereby incorporated by reference.

The present invention relates to photochromic naphthopyrans having a double-bridged terphenyl subunit and to the use thereof in plastics of all kinds, especially for ophthalmic purposes.

There has long been knowledge of various dye classes which, on irradiation with light of particular wavelengths, especially solar rays, reversibly change color. This is because these dye molecules are converted by light energy to an excited state, which they leave again in the event of interruption of the energy supply and revert to their starting state. These photochromic dyes include various pyran systems which have already been described in the prior art with different base systems and substituents.

Pyrans, specifically naphthopyrans and larger ring systems derived from these, are currently the class of photochromic compounds which has been the subject of the most work. Even though a patent was first filed as early as 1966 (U.S. Pat. No. 3,567,605), it was not until the 1990s that compounds which appeared suitable for use in spectacle lenses were developed. Suitable classes of pyran compounds are, for example, the 2,2-diaryl-2H-naphtho[1,2-b]pyrans or the 3,3-diaryl-3H-naphtho-[2,1-b]pyrans, which, in excited form, exhibit various colors, such as yellow, orange or red-orange.

A further class of photochromic compounds of interest is that of more highly fused pyrans which absorb at a longer wavelength owing to their larger ring system and give red, violet and blue hues. These may be systems derived either from the 2H-naphtho[1,2-b]pyrans or the 3H-naphtho[2,1-b]pyrans, which originate from the particular naphthopyran systems by fusion on the f side.

Diarylchromenes, especially naphthopyrans or heterocyclically fused benzopyrans, which are 6-substituted on the benzopyran by a phenyl ring or more generally an aromatic or heteroaromatic ring which is additionally bridged via the 5 position of the benzopyran via at least one carbon atom, oxygen atom or nitrogen atom, are currently the most promising photochromic compounds.

When this bridge is generated only via one atom, the result is a five-membered ring fused to the benzopyran. Examples of one carbon atom can be found in U.S. Pat. No. 5,645,767, U.S. Pat. No. 5,723,072 and U.S. Pat. No. 5,955,520, and examples of one oxygen atom in U.S. Pat. No. 6,018,059.

In U.S. Pat. No. 5,723,072, an un-, mono- or disubstituted heterocyclic ring may additionally be fused to this base system on the g, h, i, n, o or p side of the indenonaphthopyran. Accordingly, indeno[1,2-f]naphtho[1,2-b]-pyrans with a very wide range of variation of possible substituents are disclosed.

WO 96/14596, WO 99/15518, U.S. Pat. No. 5,645,767, WO 98/32037 and U.S. Pat. No. 5,698,141 disclose photochromic indenofused naphthopyran dyes derived from 2H-naphtho[1,2-b]pyran, the compositions comprising them and a process for preparation thereof. In U.S. Pat. No. 5,698,141, an un-, mono- or disubstituted heterocyclic ring may additionally be fused to this base system on the g, h, i, n, o or p side of the indenonaphthopyran. The substituent list, which is very extensive in each case, also includes quite specific spiro compounds, more particularly those systems with a spiro heterocyclic group in which, including the spiro atom at the 13 position of the base system, a 5- to 8-membered ring which always contains two oxygen atoms is present. A further embodiment of the spiro ring can be found in Japanese application 344762/2000.

When this bond is generated via two atoms, the result is a fused six-membered ring with various options solely for C, O and N. Compounds with C=O and N—R (lactam bridge) are described in U.S. Pat. No. 6,379,591. Compounds with an unsubstituted $CH_2$—$CH_2$ bridge and a fused heterocycle in the 7,8 position of the parent benzopyran are disclosed in U.S. Pat. No. 6,426,023.

U.S. Pat. No. 6,506,538 describes the carbocyclic analog compounds in which the hydrogen atoms in the bridge may be replaced by OH, ($C_1$-$C_6$)-alkoxy, or two hydrogen atoms on one carbon atom may be replaced by =O. Alternatively, one of the carbon atoms in the two-membered bridge may also be replaced by oxygen. These compounds among others are described in WO 00/02884.

When this bond is generated by three atoms, the result is a fused 7-membered ring with very many possible variations through insertion of heteroatoms. Compounds with a $CH_2$—$CH_2$—$CH_2$ bridge are described in U.S. Pat. No. 6,558,583. Here too, the hydrogen atoms in the bridge may be replaced by OH, ($C_1$-$C_6$)-alkyl or ($C_1$-$C_6$)-alkoxy, or two hydrogen atoms on one carbon atom may be replaced by =O. Given the same substitution pattern, they absorb at a shorter wavelength than the fused 6-membered rings.

US 2004/0094753 describes both compounds with a diatomic and with a triatomic bridge. The diatomic (carbon) bridge is additionally fused to a carbo- or a heterocycle. The triatomic bridge contains three carbon atoms or two carbon atoms and one oxygen atom with no additional fusion. Both rings may bear various substituents.

The different photochromic dyes available in the prior art, however, have disadvantages which, when used in sunglasses, significantly impair the wear comfort of the wearer. Firstly, the dyes have insufficiently long-wave absorption in the excited state and in the unexcited state. Secondly, there is frequently too high a thermal sensitivity of the darkening, and lightening may at the same time be too slow. Furthermore, the dyes available in the prior art often have an inadequate lifetime and hence allow only a short service life of the sunglasses. The latter becomes perceptible in rapidly declining performance and/or significant yellowing.

It is therefore an object of the present invention to provide a class of photochromic compounds which should possess significantly improved properties compared to the structures described in the prior art. These are to be found in the combination of a long-wave absorption maximum of the closed form with a steep edge to the visible wavelength range, high darkening performance, very rapid lightening reaction and very good light stability.

This object is achieved by the articles characterized in the claims.

More particularly, photochromic napthopyrans having a double-bridged terphenyl subunit with the general formula (I) are provided:

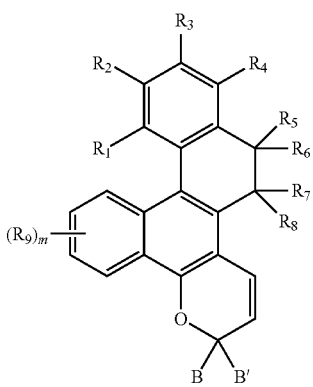

(I)

in which
at least one of the $R_2$, $R_3$ or $R_4$ radicals, preferably $R_2$ or $R_3$, is the following unit (A):

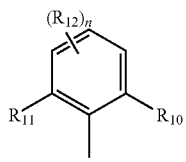

(A)

with the proviso that $R_{10}$ or $R_{11}$, together with an $R_1$, $R_2$, $R_3$ or $R_4$ radical in the ortho position to the coupling site, forms a bridge, or $R_{10}$ and $R_{11}$ form two bridges, in the case of coupling of the above (A) unit via $R_2$ in each case together with both $R_1$ and $R_3$ radicals in ortho positions to the coupling site, or in the case of coupling of the above (A) unit via $R_3$ to both $R_2$ and $R_4$ radicals in ortho positions to the coupling site, where the bridge via the $R_{10}$ or $R_{11}$ radicals in each case is one selected from the group consisting of —$CR_{13}R_{14}$—, —O—, —S—, —N(Ph)-, —N($C_1$-$C_6$ alkyl)-, —O—$CR_{13}R_{14}$—, —S—$CR_{13}R_{14}$—, —$CR_{13}R_{14}$—$CR_{13}R_{14}$—, —$CR_{15}$=$CR_{16}$— or —$CR_{15}$=N—, and in which
the $R_1$, $R_2$, $R_3$, $R_4$, $R_{10}$ and $R_{11}$ radicals, if they do not form a bridge, and also the $R_9$ and $R_{12}$ radicals, are each independently a substituent selected from the group α consisting of a hydrogen atom, a ($C_1$-$C_6$)-alkyl radical, a ($C_1$-$C_6$)-thioalkyl radical, a ($C_3$-$C_7$)-cycloalkyl radical which may have one or more heteroatoms, for example O or S, a ($C_1$-$C_6$)-alkoxy radical, a hydroxyl group, a trifluoromethyl group, bromine, chlorine, fluorine, an un-, mono- or disubstituted phenyl, phenoxy, benzyl, benzyloxy, naphthyl or naphthoxy radical, where the substituents may in turn be selected from the group α; or the $R_1$ and $R_2$ radicals in the case of coupling of the above (A) unit via $R_4$ are a fused, unsubstituted, mono- or disubstituted benzo, naphtho or pyrido ring, the substituents of which may be selected from the group α;

or two $R_9$ radicals in ortho positions to one another or two $R_{12}$ radicals in ortho positions to one another form a -D-$(CH_2)_k$- E- group or -D-$(C(CH_3)_2)_k$-E- group bonded to the aromatic ring, where k=1 or 2, where D and E are each independently selected from oxygen, sulfur, $CH_2$, $C(CH_3)_2$ or $C(C_6H_5)_2$, and where a benzo ring may in turn be fused to this -D-$(CH_2)_k$-E- group;

or two $R_9$ radicals in ortho positions to one another or two $R_{12}$ radicals in ortho positions to one another are an unsubstituted, mono- or disubstituted benzo or pyrido ring, the substituents of which may be selected from the group α;

the $R_5$, $R_6$, $R_7$ and $R_8$ radicals are each independently selected from the group α, or the $R_5$ and $R_6$ or $R_7$ and $R_8$ radicals together, including the spiro carbon atom, form a 3- to 8-membered carbo- or heteromonocyclic spiro ring which optionally bears one or more substituents from the group α, to which one to three aromatic or heteroaromatic ring systems may be fused, where the ring system is selected independently from the group β consisting of benzene, naphthalene, phenanthrene, pyridine, quinoline, furan, thiophene, pyrrole, benzofuran, benzothiophene, indole and carbazole, which may in turn be substituted by one or more substituents from the group α, where two adjacent fused ring systems may also be joined to one another by an ortho,ortho' bridge, or the $R_5$ and $R_6$ or $R_7$ and $R_8$ radicals together, including the spiro carbon atom, form a 7- to 12-membered carbobicyclic spiro ring or a 7- to 12-membered carbotricyclic spiro ring, each of which may optionally bear one or more substituents from the group α, or the $R_5$ and $R_6$ radicals together with $R_4$ are a fused unsubstituted, mono- or disubstituted benzo, naphtho or pyrido ring, the substituents of which may be selected from the group α, the $R_{13}$, $R_{14}$, $R_{15}$ and $R_{16}$ radicals are each independently a substituent selected from the group α, or the $R_{13}$ and $R_{14}$ radicals together with an $R_{12}$ radical in the meta position to the coupling site are a fused unsubstituted, mono- or disubstituted benzo, naphtho or pyrido ring, the substituents of which may be selected from the group α, though this is possible, in the case of a bridge by means of the —O—$CR_{13}R_{14}$— or —S—$CR_{13}R_{14}$— groups, only when $CR_{13}R_{14}$ is bonded directly to the phenyl ring which bears $R_{12}$, or in the case of coupling of the above (A) unit via $R_3$ and a bridge via $R_2$, the $R_{13}$ and $R_{14}$ radicals together with $R_1$, or in the case of coupling of the above (A) unit via $R_4$ and a bridge via $R_3$, the $R_{13}$ and $R_{14}$ radicals together with $R_2$, or in the case of coupling of the above (A) unit via $R_2$ and a bridge via $R_3$, the $R_{13}$ and $R_{14}$ radicals together with $R_4$, are a fused unsubstituted, mono- or disubstituted benzo, naphtho or pyrido ring, the substituents of which may be selected from the group α, or in the case of coupling of the above (A) unit via $R_3$ and a bridge via $R_4$, the $R_{13}$ and $R_{14}$ radicals together with $R_5$ and $R_6$ are a fused unsubstituted, mono- or disubstituted benzo, naphtho or pyrido ring, the substituents of which may be selected from the group α, though this is possible, in the case of a bridge by means of the —O—$CR_{13}R_{14}$— or —S—$CR_{13}R_{14}$— groups, only when $CR_{13}R_{14}$ is bonded directly to the phenyl ring which also bears $CR_5R_6$, or the $R_{15}$ and $R_{16}$ radicals are a fused unsubstituted, mono- or disubstituted benzo, naphtho or pyrido ring, the substituents of which may be selected from the group α;

m is 0, 1, 2, 3 or 4, and n is 0, 1, 2 or 3;

B and B' are each independently selected from one of the following groups a), b) and c):
a) mono-, di- and trisubstituted aryl radicals, where the aryl radical is phenyl, naphthyl or phenanthryl;
b) unsubstituted, mono- and disubstituted heteroaryl radicals, where the heteroaryl radical is pyridyl, furanyl, benzofuranyl, thienyl, benzothienyl, 1,2,3,4-tetrahydrocarbazolyl or julolidinyl; where the substituents of the aryl or heteroaryl radicals in a) and b) are those selected from the above-defined group α or from the group χ consisting of hydroxyl, 2-phenylethenyl un-, mono- or disubstituted on the phenyl ring, (phenylimino)methylene un-, mono- or disubstituted on the phenyl ring, (phenylmethylene)imino un-, mono- or disubstituted on the phenyl ring, amino, mono-$(C_2$-$C_6)$-alkylamino, di-$(C_2$-$C_6)$-alkylamino, mono- and diphenylamino un-, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenzo[b,f]azepinyl, where the substituent(s) may each independently in turn be selected from $(C_1$-$C_6)$-alkyl, $(C_1$-$C_6)$-alkoxy, bromine, chlorine and fluorine;

or where two directly adjacent substituents are a Y—$(CX_2)_p$—Z— moiety where p=1, 2 or 3, X may be hydrogen, $CH_3$ or $C_6H_5$, and Y and Z may each independently be oxygen, sulfur, N—$(C_1$-$C_6)$-alkyl, N—$C_6H_5$, $CH_2$, $C(CH_3)_2$ or $C(C_6H_5)_2$, where two or more adjacent carbon atoms in this Y—$(CX_2)_p$—Z— moiety may each independently also be part of a benzo ring system fused thereto, which may in each case in turn have one or more substituents selected from the group α or the group χ; or c) B and B' together with the adjacent carbon atom of the pyran ring form an un-, mono- or disubstituted 9,10-dihydroanthracene, fluorene, thioxanthene, xanthene, benzo[b]fluorene, 5H-dibenzo[a,d]cycloheptene or dibenzosuberone radical, or a saturated hydrocarbon radical which is $(C_3$-$C_{12})$-spiromonocyclic, $(C_7$-$C_{12})$-spirobicyclic or $(C_7$-$C_{12})$-spirotricyclic, where the substituents of the unsaturated cycles may each independently be selected from the group α or the group χ.

The inventive photochromic naphthopyrans having a double-bridged terphenyl subunit have, in comparison to systems currently available in the prior art, an improved profile of properties, in particular an improved combination of very good lifetime and high lightening speed. The inventive compounds feature a balance of long-wave absorption maximum, high darkening performance, very fast lightening reaction and very good light stability.

The $R_5$ and $R_6$ or $R_7$ and $R_8$ radicals may together, including the spiro carbon atom, form a 3- to 8-membered carbo- or heterocyclic ring to which one to three aromatic or heteroaromatic ring systems may be fused, where the ring system is selected from the group β consisting of benzene, naphthalene, phenanthrene, pyridine, quinoline, furan, thiophene, pyrrole, benzofuran, benzothiophene, indole and carbazole, which may in turn be substituted by one or more substituents from the group α. It is also possible for two adjacent fused ring systems to be joined to one another by an ortho,ortho' bridge, preferably an ethylene or a 1,2-ethenediyl bridge, such that, for example, the following structural unit is present in the latter case:

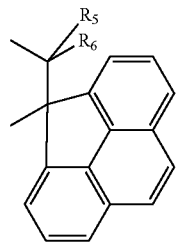

In a preferred embodiment, however, the $R_5$ and $R_6$ or $R_7$ and $R_8$ radicals are each independently selected from the group α.

When B or B' is a saturated hydrocarbon radical which is $C_3$-$C_{12}$-spiromonocyclic, $C_7$-$C_{12}$-spirobicyclic or $C_7$-$C_{12}$-spirotricyclic, $C_3$-$C_{12}$-spiromonocyclic is understood to mean a 3- to 12-membered ring as familiar to the person skilled in the art. $C_7$-$C_{12}$-Spirobicyclic systems are also well known to a person skilled in the art. Examples here in turn include norbornane, norbornene, 2,5-norbornadiene, norcarane and pinane. An illustrative $C_7$-$C_{12}$-spirotricyclic system is adamantane.

In a further preferred embodiment, the B and B' radicals are each independently selected from group a) as defined above.

The substituents of the group χ which have nitrogen atoms or bear amine groups are bonded via the latter to the phenyl, naphthyl or phenanthryl radical of group a).

With regard to the substituents of the group χ which may be bonded to the phenyl, naphthyl or phenanthryl radical of group a) or the B or B' radicals, when two or more adjacent carbon atoms of this Y—$(CX_2)_p$—Z— moiety may each independently be part of a benzo ring system fused thereto, this means that the two methylene carbon atoms (—$CH_2$—$CH_2$—) may then become part of a fused ring system. When, for example, two or there benzo rings are fused, it is possible, for example, for the following structural units as shown below to be present:

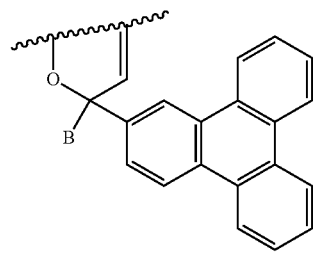

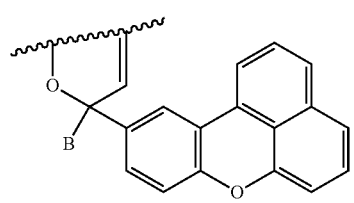

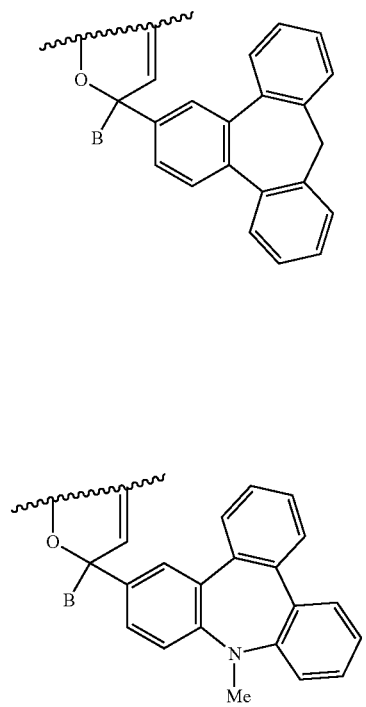

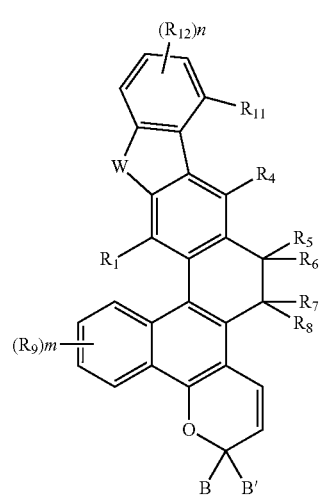

It will be appreciated, however, that it is also possible for only one benzo ring fused via two adjacent carbon atoms of this Y—(CX$_2$)$_p$—Z— moiety to be present.

Preferred photochromic naphthopyrans having a double-bridged terphenyl subunit according to the present invention have the following general formulae (II) and (III):

(II)

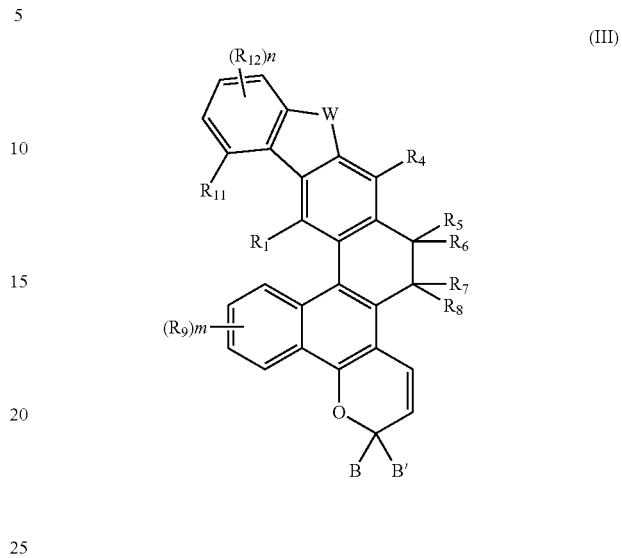

(III)

in which m, n, B, B', R$_1$ and R$_4$ to R$_{12}$ are each as defined above and W symbolizes the bridge specified above (the bridge is formed in these two cases by the R$_2$ and R$_{10}$ radicals and is as defined above, i.e. selected from the group consisting of —CR$_{13}$R$_{14}$—, —O—, —S—, —N(Ph)-, —N (C$_1$-C$_6$ alkyl)-, —O—CR$_{13}$R$_{14}$—, —S—CR$_{13}$R$_{14}$—, —CR$_{13}$R$_{14}$—CR$_{13}$R$_{14}$—, —CR$_{15}$=CR$_{16}$— or —CR$_{15}$=N—).

Compared to the prior art, i.e. U.S. Pat. No. 6,506,538, the inventive compounds—given the same other substituents B, B', R$_1$ and R$_4$ to R$_9$ have a longer-wave and in particular hyperchromic (more intense) absorption band both in the unexcited and in the excited state. A longer-wave and more intense absorption in the unexcited state has two important advantages in the introduction of the photochromic dyes, for example, into plastic spectacle lenses. Firstly, the inventive compounds also react when, under unfavorable atmospheric conditions, only very long-wave UV sunlight (from 380 nm) is incident. It is evident from FIG. 1 that the inventive compounds in the unexcited form absorb significantly more intensely at wavelengths greater than 370 nm compared to prior art compounds. As a result, the inventive photochromic compounds, even under unfavorable conditions, exhibit very good darkening performance. Secondly, full UV protection up to 400 nm is achieved automatically as a result, since the inventive compounds completely absorb the incident UV light. There is no need to add UV absorbers in the production of sunglasses. This is an important advantage since added UV absorbers always absorb some of the incident light, such that lenses containing UV absorbers always darken to a lesser degree than without UV absorbers.

The structure of the inventive compounds shown in FIG. 1 and the longest-wave absorption maxima thereof in the excited form are shown in table 1 below (compared to the prior art from U.S. Pat. No. 6,506,538):

TABLE 1

Longest-wave absorption maxima in the excited state

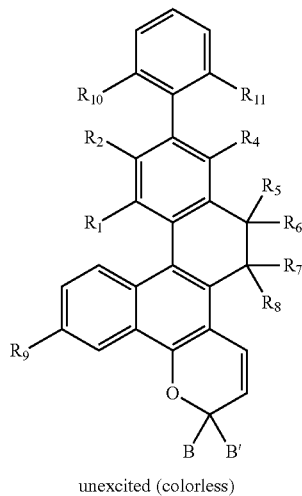

unexcited (colorless)

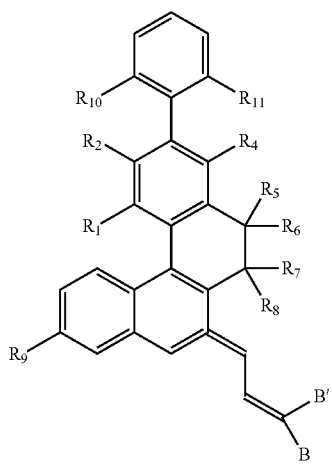

excited (colored)

A) Prior art (U.S. Pat. No. 6,506,538)

| $R_1$ | $R_2$ | $R_{10}$ | $R_{11}$ | $R_4$ | $R_5$ | $R_6$ | $R_7$ | $R_8$ | $R_9$ | B | B' | $\lambda_{max}$ (excited) |
|---|---|---|---|---|---|---|---|---|---|---|---|---|
| H | H | H | H | H | H | H | H | H | OMe | Phenyl | 4-(N-Morpholinyl)phenyl | 575 nm |

B) Inventive compounds

| | $R_1$ | $R_2$ | $R_{10}$ | $R_{11}$ | $R_4$ | $R_5$ | $R_6$ | $R_7$ | $R_8$ | $R_9$ | B | B' | $\lambda_{max}$ (excited) |
|---|---|---|---|---|---|---|---|---|---|---|---|---|---|
| 1) | H | —O— | | H | H | H | H | H | H | OMe | Phenyl | 4-(N-Morpholinyl)phenyl | 595 nm |
| 2) | H | —S— | | H | H | H | H | H | H | OMe | Phenyl | 4-(N-Morpholinyl)phenyl | 590 nm |
| 3) | H | —SO$_2$— | | H | H | H | H | H | H | OMe | Phenyl | 4-(N-Morpholinyl)phenyl | 595 nm |
| 4) | H | —CH=CH— | —CH=CH— | | H | H | H | H | H | OMe | Phenyl | 4-(N-Morpholinyl)phenyl | 590 nm |

To measure the properties of the inventive photochromic dyes and of the prior art compound (see above), 500 ppm of each dye were dissolved in an acrylate monomer matrix and, after addition of a polymerization initiator, thermally polymerized with the aid of a temperature program. The transmission properties of the plastic lenses thus produced (thickness 2 mm) were subsequently analyzed to DIN EN ISO 8980-3.

The inventive compounds can be used in polymer materials or plastics articles of any kind and form for a multitude of end uses for which photochromic behavior is of significance. A dye according to the present invention or a mixture of such dyes can be used. For example, the inventive photochromic naphthopyrans having a double-bridged terphenyl subunit can be used in lenses, especially ophthalmic lenses, lenses for spectacles and goggles of all kinds, for example ski goggles, sunglasses, motorcycle goggles, visors of protective helmets, and the like. In addition, the inventive photochromic naphthopyrans having a double-bridged terphenyl subunit can also be used, for example, as sun protection in vehicles and living spaces, in the form of windows, protective screens, covers, roofs or the like.

To produce such photochromic articles, the inventive photochromic naphthopyrans having a double-bridged terphenyl subunit can be applied to a polymer material, such as an organic polymer material, or be embedded therein, by various processes described in the prior art as already specified in WO 99/15518.

A distinction can be drawn between bulk coloring and surface coloring processes. A bulk coloring process comprises, for example, the dissolution or dispersion of the photochromic compound or compounds according to the present invention in a polymer material, for example by the addition of the photochromic compound(s) to a monomeric material before polymerization is effected. A further means of producing a photochromic article is the penetration of the polymer material(s) with the photochromic compound(s) by immersing the polymer material into a hot solution of the photochromic dye(s) according to the present invention or else, for example, a thermal transfer process. The photochromic compound(s) may also be provided, for example, in the form of a separate layer between adjacent layers of the polymer material, for example as part of a polymeric film. In addition, it is also possible to apply the photochromic compound(s) as part of a coating present on the surface of the polymer material. The expression "penetration" in this context shall mean the migration of the photochromic compound(s) into the polymer material, for example by the solvent-supported transfer of the photochromic compound(s) into a polymer matrix, vapor phase transfer or other surface diffusion processes of this kind. Advantageously, it is possible to produce such photochromic articles, for example spectacle lenses, not only by means of customary bulk coloring, but also in the same way by means of surface coloring, it being possible to achieve a surprisingly relatively low migration tendency in the case of the latter variant. This is advantageous in particular in the case of subsequent finishing steps, since—for example in the case of an antireflection coating, as a result of the lesser back-diffusion under reduced pressure—layer detachment and similar defects are reduced drastically.

Overall, based on the inventive photochromic naphthopyrans having a double-bridged terphenyl subunit, it is possible to apply or to embed colorings, i.e. dyes, of any compatibility (compatible from a chemical point of view and in terms of color) to or into the polymer material, in order to satisfy both esthetic aspects and medical or fashion aspects. The specifically selected dye(s) may accordingly vary depending on the intended effects and requirements.

Figure 2:
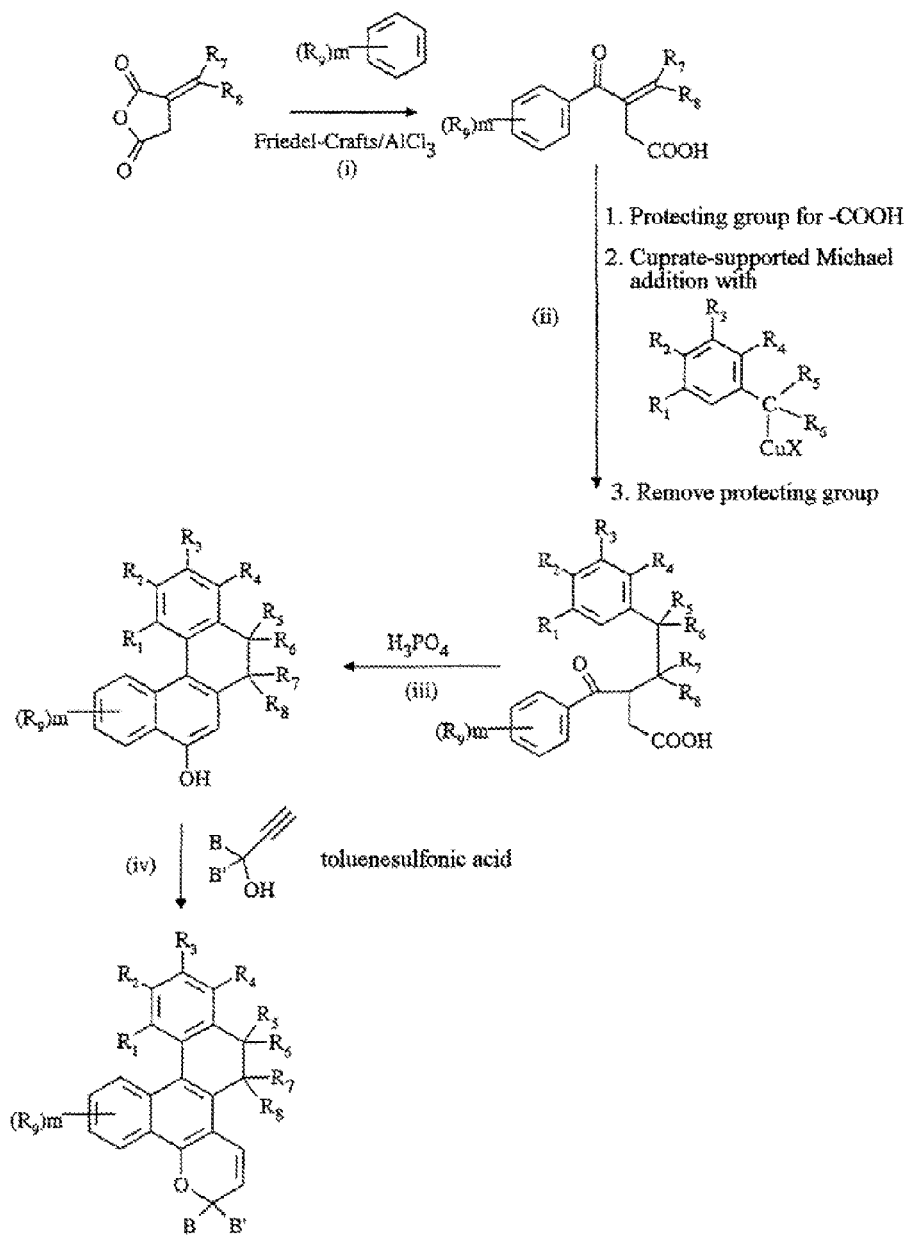

The inventive photochromic compounds can be prepared according to the illustrative synthesis scheme which follows, as shown in FIG. 2.

Suitably substituted methylidenesuccinic anhydrides are subjected in a first step to a Friedel-Crafts reaction with suitably substituted benzene derivatives (step (i)). The —COOH group of the resulting intermediate is subsequently protected and this intermediate is subjected to a cuprate-supported Michael addition with correspondingly substituted benzyl derivatives (step (ii)). After removal of the carboxylic acid protecting group, correspondingly substituted 9,10-dihydrophenanthrene derivatives are formed via intramolecular cyclization by means of phosphoric acid (step (iii)). Subsequently, these substituted dihydrophenanthrene derivatives are reacted with suitably substituted 2-propyn-1-ol derivatives in step (iv) to give the inventive compounds.

The invention claimed is:
1. Photochromic naphthopyran having a double-bridged terphenyl subunit and having the general formula (I):

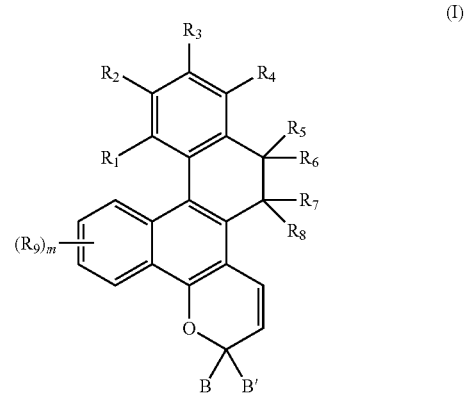

(I)

in which
at least one of the $R_2$, $R_3$ or $R_4$ radicals is the following unit (A):

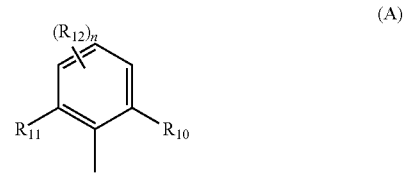

(A)

with the proviso that $R_{10}$ or $R_{11}$, together with an $R_1$, $R_2$, $R_3$ or $R_4$ radical in the ortho position to the coupling site, forms a bridge, or $R_{10}$ and $R_{11}$ form two bridges, in the case of coupling of the above (A) unit via $R_2$ in each case together with both $R_1$ and $R_3$ radicals in ortho positions to the coupling site, or in the case of coupling of the above (A) unit via $R_3$ to both $R_2$ and $R_4$ radicals in ortho positions to the coupling site, where the bridge via the $R_{10}$ or $R_{11}$ radicals in each case is one selected from the group consisting of —$CR_{13}R_{14}$—, —O—, —S—, —N(Ph)-, —N($C_1$-$C_6$ alkyl)-, —O—$CR_{13}R_{14}$—, —S—$CR_{13}R_{14}$—, —$CR_{13}R_{14}$—$CR_{13}R_{14}$—, —$CR_{15}$=$CR_{16}$— or —$CR_{15}$=N—,
and in which
the $R_1$, $R_2$, $R_3$, $R_4$, $R_{10}$ and $R_{11}$ radicals, if they do not form a bridge, and also the $R_9$ and $R_{12}$ radicals, are each independently a substituent selected from the group α consisting of a hydrogen atom, a ($C_1$-$C_6$)-alkyl radical, a ($C_1$-$C_6$)-thioalkyl radical, a ($C_3$-$C_7$)-cycloalkyl radical which may have one or more heteroatoms, for example O or S, a ($C_1$-$C_6$)-alkoxy radical, a hydroxyl group, a trifluoromethyl group, bromine, chlorine, fluorine, an un-, mono- or disubstituted phenyl, phenoxy, benzyl, benzyloxy, naphthyl or naphthoxy radical, where the substituents may in turn be selected from the group α; or the $R_1$ and $R_2$ radicals in the case of coupling of the above (A) unit via $R_4$ are a fused, unsubstituted, mono- or disubstituted benzo, naphtho or pyrido ring, the substituents of which may be selected from the group α;

or two $R_9$ radicals in ortho positions to one another or two $R_{12}$ radicals in ortho positions to one another form a -D-$(CH_2)_k$-E- group or -D-$(C(CH_3)_2)_k$-E- group bonded to the aromatic ring, where k=1 or 2, where D and E are each independently selected from oxygen, sulfur, $CH_2$, $C(CH_3)_2$ or $C(C_6H_5)_2$, and where a benzo ring may in turn be fused to this -D-$(CH_2)_k$-E- group;

or two $R_9$ radicals in ortho positions to one another or two $R_{12}$ radicals in ortho positions to one another are an unsubstituted, mono- or disubstituted benzo or pyrido ring, the substituents of which may be selected from the group α, or the $R_5$, $R_6$, $R_7$ and $R_8$ radicals are each independently selected from the group α, or the $R_5$ and $R_6$ or $R_7$ and $R_8$ radicals together, including the spiro carbon atom, form a 3- to 8-membered carbo- or heteromonocyclic spiro ring which optionally bears one or more substituents from the group α, to which one to three aromatic or heteroaromatic ring systems may be fused, where the ring system is selected independently from the group β consisting of benzene, naphthalene, phenanthrene, pyridine, quinoline, furan, thiophene, pyrrole, benzofuran, benzothiophene, indozole and carbazole, which may in turn be substituted by one or more substituents from the group α, where two adjacent fused ring systems may also be joined to one another by an ortho,ortho' bridge, or the $R_5$ and $R_6$ or $R_7$ and $R_8$ radicals together, including the spiro carbon atom, form a 7- to 12-membered carbobicyclic spiro ring or a 7- to 12-membered carbotricyclic spiro ring, each of which may optionally bear one or more substituents from the group α, or the $R_5$ and $R_6$ radicals together with $R_4$ are a fused unsubstituted, mono- or disubstituted benzo, naphtho or pyrido ring, the substituents of which may be selected from the group α, the $R_{13}$, $R_{14}$, $R_{15}$ and $R_{16}$ radicals are each independently a substituent selected from the group α, or the $R_{13}$ and $R_{14}$ radicals together with an $R_{12}$ radical in the meta position to the coupling site are a fused unsubstituted, mono- or disubstituted benzo, naphtho or pyrido ring, the substituents of which may be selected from the group α, though this is possible, in the case of a bridge by means of the —O—$CR_{13}R_{14}$— or —S—$CR_{13}R_{14}$— groups, only when $CR_{13}R_{14}$ is bonded directly to the phenyl ring which bears $R_{12}$, or in the case of coupling of the above (A) unit via $R_3$ and a bridge via $R_2$, the $R_{13}$ and $R_{14}$ radicals together with $R_1$, or in the case of coupling of the above (A) unit via $R_4$ and a bridge via $R_3$, the $R_{13}$ and $R_{14}$ radicals together with $R_2$, or in the case of coupling of the above (A) unit via $R_2$ and a bridge via $R_3$, the $R_{13}$ and $R_{14}$ radicals together with $R_4$, are a fused unsubstituted, mono- or disubstituted benzo, naphtho or pyrido ring, the substituents of which may be selected from the group α, or in the case of coupling of the above (A) unit via $R_3$ and a bridge via $R_4$, the $R_{13}$ and $R_{14}$ radicals together with $R_5$ and $R_6$ are a fused unsubstituted, mono- or disubstituted benzo, naphtho or pyrido ring, the substituents of which may be selected from the group α, though this is possible, in the case of a bridge by means of the —O—$CR_{13}R_{14}$— or —S—$CR_{13}R_{14}$— groups, only when $CR_{13}R_{14}$ is bonded directly to the phenyl ring which also bears $CR_5R_6$, or the $R_{15}$ and $R_{16}$ radicals are a fused unsubstituted, mono- or disubstituted benzo, naphtho or pyrido ring, the substituents of which may be selected from the group α;

m is 0, 1, 2, 3 or 4, and n is 0, 1, 2 or 3;

B and B' are each independently selected from one of the following groups a), b) and c):
a) mono-, di- and trisubstituted aryl radicals, where the aryl radical is phenyl, naphthyl or phenanthryl;
b) unsubstituted, mono- and disubstituted heteroaryl radicals, where the heteroaryl radical is pyridyl, furanyl, benzofuranyl, thienyl, benzothienyl, 1,2,3,4-tetrahydrocarbazolyl or julolidinyl;
where the substituents of the aryl or heteroaryl radicals in a) and b) are those selected from the above-defined group α or from the group χ consisting of hydroxyl, 2-phenylethenyl un-, mono- or disubstituted on the phenyl ring, (phenylimino)methylene un-, mono- or disubstituted on the phenyl ring, (phenylmethylene)imino un-, mono- or disubstituted on the phenyl ring, amino, mono-$(C_1-C_6)$-alkylamino, di-$(C_1-C_6)$-alkylamino, mono- and diphenylamino un-, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenzo[b,f]azepinyl, where the substituent(s) may each independently in turn be selected from $(C_1-C_6)$-alkyl, $(C_1-C_6)$-alkoxy, bromine, chlorine and fluorine;
or where two directly adjacent substituents are a Y—$(CX_2)_p$—Z— moiety where p=1, 2 or 3, X may be hydrogen, $CH_3$ or $C_6H_5$, and Y and Z may each independently be oxygen, sulfur, N—$(C_1-C_6)$-alkyl, N—$C_6H_5$, $CH_2$, $C(CH_3)_2$ or $C(C_6H_5)_2$, where two or more adjacent carbon atoms in this Y—$(CX_2)_p$—Z— moiety may each independently also be part of a benzo ring system fused thereto, which may in each case in turn have one or more substituents selected from the group α or the group χ;
or
c) B and B' together with the adjacent carbon atom of the pyran ring form an un-, mono- or disubstituted 9,10-dihydroanthracene, fluorene, thioxanthene, xanthene, benzo[b]fluorene, 5H-dibenzo[a,d]cycloheptene or dibenzosuberone radical, or a saturated hydrocarbon radical which is $(C_3-C_{12})$-spiromonocyclic, $(C_7-C_{12})$-spirobicyclic or $(C_7-C_{12})$-spirotricyclic, where the substituents of the unsaturated cycles may each independently be selected from the group α or the group χ.

2. Photochromic naphthopyrans having a double-bridged terphenyl subunit as claimed in claim 1, where the $R_5$, $R_6$, $R_7$ and $R_8$ radicals are each independently selected from the group α.

3. Photochromic naphthopyrans having a double-bridged terphenyl subunit as claimed in claim 2, where B and B' are each independently selected from group a).

4. Photochromic naphthopyrans having a double-bridged terphenyl subunit as claimed in claim 2, where the $R_{13}$, $R_{14}$, $R_{15}$ and $R_{16}$ radicals are each independently selected from the group α.

5. Photochromic naphthopyrans having a double-bridged terphenyl subunit as claimed in claim 2 which have the following general formulae (II) and (III):

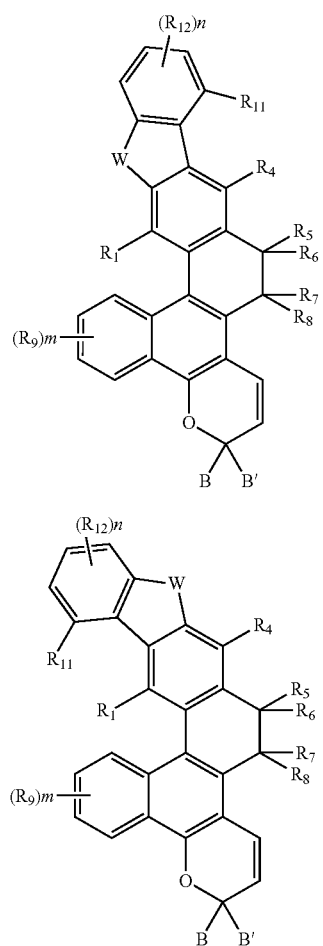

in which m, n, B, B', $R_1$ and also $R_4$ to $R_{12}$ are each as defined above, and W symbolizes the bridge specified above.

6. A process comprising compounding in or applying on a polymer material the photochromic naphthopyrans having a double-bridged terphenyl subunit as claimed in claim 2.

7. Photochromic naphthopyrans having a double-bridged terphenyl subunit as claimed in claim 1, where B and B' are each independently selected from group a).

8. Photochromic naphthopyrans having a double-bridged terphenyl subunit as claimed in claim 7, where the $R_{13}$, $R_{14}$, $R_{15}$ and $R_{16}$ radicals are each independently selected from the group α.

9. Photochromic naphthopyrans having a double-bridged terphenyl subunit as claimed in claim 7 which have the following general formulae (II) and (III):

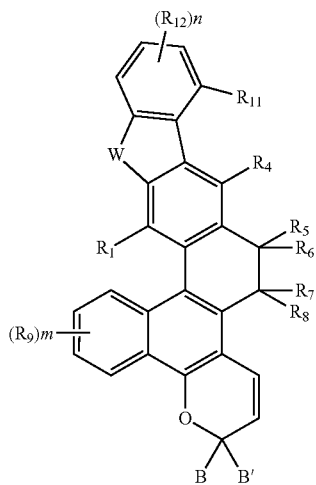

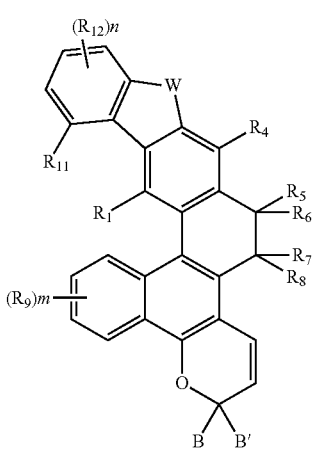

in which m, n, B, B', $R_1$ and also $R_4$ to $R_{12}$ are each as defined above, and W symbolizes the bridge specified above.

10. A process comprising compounding in or applying on a polymer material the photochromic naphthopyrans having a double-bridged terphenyl subunit as claimed in claim 7.

11. Photochromic naphthopyrans having a double-bridged terphenyl subunit as claimed in claim 7, where the $R_5$, $R_6$, $R_7$ and $R_8$ radicals are each independently selected from the group α.

12. Photochromic naphthopyrans having a double-bridged terphenyl subunit as claimed in claim 11, where the $R_{13}$, $R_{14}$, $R_{15}$ and $R_{16}$ radicals are each independently selected from the group α.

13. Photochromic naphthopyrans having a double-bridged terphenyl subunit as claimed in claim 11 which have the following general formulae (II) and (III):

(II)

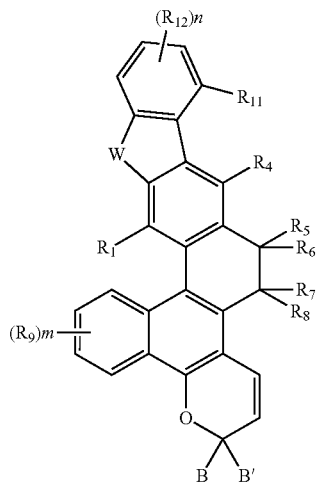

(III)

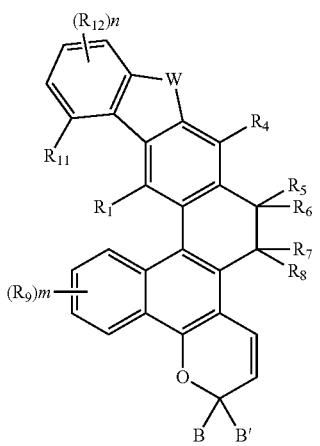

in which m, n, B, B', $R_1$ and also $R_4$ to $R_{12}$ are each as defined above, and W symbolizes the bridge specified above.

14. A process comprising compounding in or applying on a polymer material the photochromic naphthopyrans having a double-bridged terphenyl subunit as claimed in claim 11.

15. Photochromic naphthopyrans having a double-bridged terphenyl subunit as claimed in claim 1, where the $R_{13}$, $R_{14}$, $R_{15}$ and $R_{16}$ radicals are each independently selected from the group α.

16. Photochromic naphthopyrans having a double-bridged terphenyl subunit as claimed in claim 15 which have the following general formulae (II) and (III):

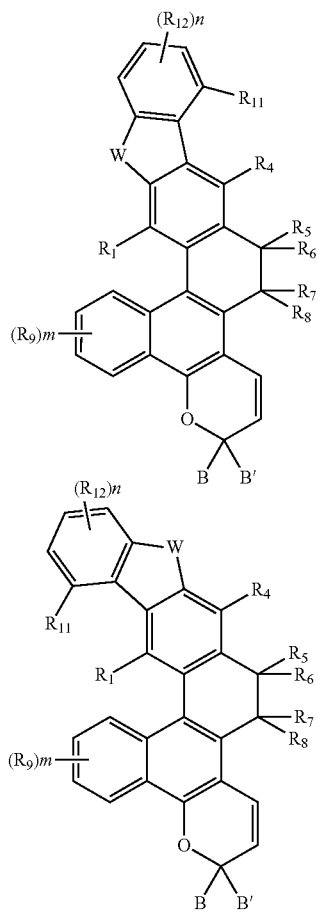

in which m, n, B, B', $R_1$ and also $R_4$ to $R_{12}$ are each as defined above, and W symbolizes the bridge specified above.

17. A process comprising compounding in or applying on a polymer material the photochromic naphthopyrans having a double-bridged terphenyl subunit as claimed in claim 15.

18. Photochromic naphthopyrans having a double-bridged terphenyl subunit as claimed in claim 1 which have the following general formulae (II) and (III):

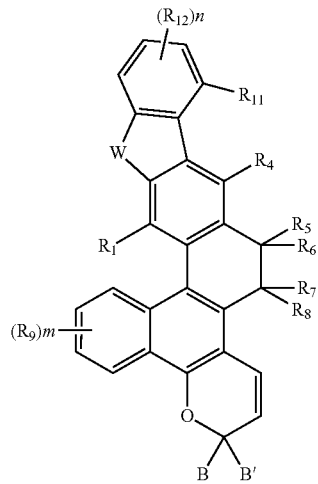

-continued

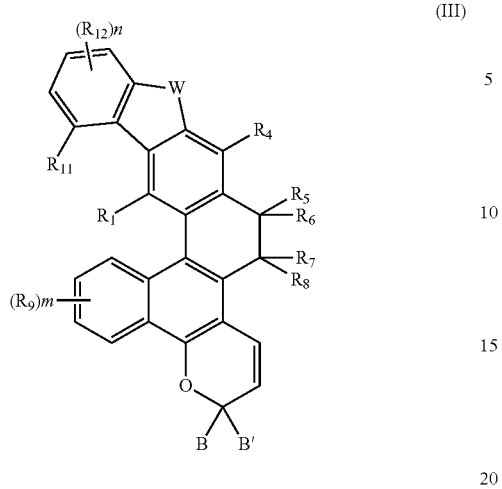

(III)

in which m, n, B, B', $R_1$ and also $R_4$ to $R_{12}$ are each as defined above, and W symbolizes the bridge specified above.

19. A process comprising compounding in or applying on a polymer material the photochromic naphthopyrans having a double-bridged terphenyl subunit as claimed in claim 1.

20. The process as claimed in claim 19, wherein the polymer material is an ophthalmic lens.

\* \* \* \* \*

UNITED STATES PATENT AND TRADEMARK OFFICE
CERTIFICATE OF CORRECTION

PATENT NO. : 8,486,312 B2
APPLICATION NO. : 12/937414
DATED : July 16, 2013
INVENTOR(S) : Melzig et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this
Eighth Day of September, 2015

Michelle K. Lee
*Director of the United States Patent and Trademark Office*